United States Patent
Fujii et al.

(10) Patent No.: US 8,739,971 B2
(45) Date of Patent: Jun. 3, 2014

(54) STOPPER STORAGE CASE

(75) Inventors: Naoto Fujii, Tokyo (JP); Hirotaka Yoshihara, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/246,373

(22) Filed: Sep. 27, 2011

(65) Prior Publication Data
US 2012/0074011 A1  Mar. 29, 2012

(30) Foreign Application Priority Data

Sep. 27, 2010  (JP) .................................. 2010-215254

(51) Int. Cl.
    *B65D 83/10* (2006.01)
(52) U.S. Cl.
    USPC .......................................... 206/369; 206/368
(58) Field of Classification Search
    USPC ........................... 206/369, 368, 379, 443, 583
    See application file for complete search history.

(56) References Cited

U.S. PATENT DOCUMENTS

| | | | |
|---|---|---|---|
| 2,371,433 A | 3/1945 | Davis | |
| 4,382,788 A | 5/1983 | Pelerin | |
| 5,788,488 A | 8/1998 | Grossman | |
| 5,829,590 A | 11/1998 | Klein | |
| 5,959,221 A * | 9/1999 | Boyd et al. | 73/864.24 |
| 5,967,318 A * | 10/1999 | Rosler | 206/372 |
| D432,790 S * | 10/2000 | Streich et al. | D3/318 |
| 6,358,049 B1 | 3/2002 | Cerniway | |
| 6,360,892 B1 * | 3/2002 | Chen | 206/376 |
| 7,000,785 B2 * | 2/2006 | Jafari et al. | 211/74 |
| 7,401,700 B2 * | 7/2008 | Dost et al. | 206/379 |
| 2004/0178101 A1 | 9/2004 | Wang | |
| 2004/0200749 A1 * | 10/2004 | Wang | 206/373 |
| 2006/0264822 A1 * | 11/2006 | Nagamatsu | 604/97.02 |
| 2010/0028828 A1 * | 2/2010 | Vogel et al. | 433/77 |

FOREIGN PATENT DOCUMENTS

| | | |
|---|---|---|
| DE | 297 20 294 U1 | 12/1998 |
| FR | 2.196.587 A5 | 3/1974 |
| JP | 2003-501135 A | 1/2003 |
| WO | WO 00/74585 A2 | 12/2000 |

OTHER PUBLICATIONS

Extended European Search Report issued Sep. 25, 2013 in European Patent Application No. 11007846.6.

* cited by examiner

*Primary Examiner* — Anthony Stashick
*Assistant Examiner* — Ernesto Grano
(74) *Attorney, Agent, or Firm* — Oblon, Spivak, McClelland, Maier & Neustadt, L.L.P.

(57) ABSTRACT

A stopper storage case has openings and drill blade insertion paths. The openings are large enough to allow a spring-like engagement portion of the stopper to pass. Each drill blade insertion path is large enough to allow a drill blade to pass. Concave parts extend from the respective openings to the drill blade insertion paths and can store stoppers of different lengths. Each of the concave parts has a protrusion to be engaged in a groove in the outer peripheral surface of the stopper. Stopper holding overhangs formed at the top of each concave part are elastic enough not to interfere with insertion of the stopper from above into the concave part and removal of the stopper from inside the concave part.

9 Claims, 3 Drawing Sheets

STOPPER STORAGE CASE

BACKGROUND OF THE INVENTION

1. Field of the Invention

The present invention relates to a stopper storage case capable of storing in parallel a plurality of stoppers each formed as a cylinder in which a drill, used in dental implant treatment to bore a hole in which a dental implant fixture is to be embedded (this hole will be referred to as "dental implant fixture embedding hole" hereunder) in the jawbone to a predetermined depth, is to be fitted first at the free end of the blade thereof, the stopper including a spring-like engagement portion which is to be engaged on a projecting flange provided on a shank of the drill to thereby define a penetration depth of the drill. Also the stopper storage case facilitates easy attachment and detachment of the stopper to and from the drill installed to a dental handpiece, and can preferably be washed, sterilized and autoclaved sterilized while storing therein the stoppers having been used.

2. Description of the Prior Art

In the recent field of dental prosthetics, there has been prevailing a dental implant treatment in which a dental implant fixture formed from titanium or titanium alloy excellent in biological affinity is embedded in a portion of the jawbone corresponding to a missing tooth and used as a substitute for the missing natural dental root via the process of a direct integration of the prosthesis with the bone, called "osseointegration". The dental implant fixtures used in the dental implant surgery include two types, of which one is formed separately from an abutment as another part of a dental implant on which a dental prosthesis is to be fixed, and the other is formed integrally with an abutment.

Each of the dental implant fixtures of these types has to be embedded to a predetermined depth in the jawbone. To this end, a stopper to define a depth of drill penetration is conventionally installed on a drill which is used to bore a dental implant fixture embedding hole in the jawbone. In this case, the stopper is installed in a predetermined position on the blade of the drill with a screw or the like as disclosed in the Japanese Published Unexamined Application No. 501135 of 2003, for example. However, such a method is troublesome since it is required to adjust the position of installation of the stopper at each time of installation. Also, if the screw is not tightened securely, a trouble such as shift of the stopper takes place.

In these circumstances, the Inventors of the present invention have found that it is preferable to form a projecting flange integrally on a shank of a dental drill which is to be used to bore a dental implant fixture embedding hole in the jawbone to a predetermined depth in dental implant treatment and engage on the flange a spring-like engagement portion of on a stopper which is to define a penetration depth of the drill blade, since there occurs advantageously no such trouble as the shift of the stopper as in case the stopper is fixed to the drill with a screw since the flange is provided integrally on the drill shank.

By forming the flange integrally on the shank of the drill and preparing a plurality of stoppers each formed as a cylinder in which the drill first is to be fitted at the free end of the blade thereof, the stopper including a spring-like engagement portion to be engaged on the projecting flange provided on the drill shank and being destined to define a penetration depth of the drill, it is possible to define a penetration depth of the drill blade easily. However, the spring-like engagement portion of the stopper once engaged on the projecting flange on the drill shank should not easily be disengageable from the flange. That is, a strong force is required to engage the spring-like engagement portion of the stopper onto the drill flange and disengage the former from the latter. Further, these stoppers are so small that they will get scattered and lost at the time of storing, washing, sterilization or autoclaved sterilization.

SUMMARY OF THE INVENTION

It is therefore desirable to overcome the above-mentioned drawbacks of the prior art by providing a stopper storage case capable of storing in parallel a plurality of stoppers prepared as above, facilitating easy attachment and detachment of the stopper to and from the drill installed to a dental handpiece, and which can preferably be washed, sterilized and autoclaved sterilized while stoppers having been used in a dental surgery are being kept stored therein.

The Inventors of the present invention have devoted themselves to solve the aforementioned problems. As the result, they have worked out the present invention by having found that with a stopper storage case for storing in parallel a plurality of stoppers each formed as a cylinder in which a drill, used in dental implant treatment to bore a dental implant fixture embedding hole in the jawbone, is to be fitted first at the free end of the blade thereof, the stopper including a spring-like engagement portion which is to be engaged on a projecting flange provided on a shank of the drill to thereby define a penetration depth of the drill, the stopper storage case having openings formed therein at one end thereof, each being large enough to allow the spring-like engagement portion of the stopper to pass; drill blade insertion paths formed at the other end thereof to be open at the top thereof, each being large enough to allow the drill blade to pass; concave parts formed therein extending from the respective opening to the drill blade insertion path and being capable of storing stoppers different in length from each other respectively; a protrusion formed in each of the concave parts to be engaged in a groove formed in the outer peripheral surface of the stopper; and stopper holding overhangs formed at the top of each concave part and which is elastic enough not to interfere with insertion of the stopper from above into the concave part and removal of the stopper from inside the concave part to above, it is possible to store unused stoppers stably not to let them go out thereof and permit to attach and detach the stopper to and from the drill inside the stopper storage case itself. Thus, the user of this stopper storage case will not lose the stoppers and can easily select among the stoppers one which defines a desired penetration depth of the drill.

According an embodiment of the present invention, there is provided a stopper storage case for storing in parallel a plurality of stoppers each formed as a cylinder in which a drill, used in dental implant treatment to bore a dental implant fixture embedding hole in the jawbone, is to be fitted first at the free end of the blade thereof, the stopper including a spring-like engagement portion which is to be engaged on a projecting flange provided on a shank of the drill to thereby define a penetration depth of the drill, the stopper storage case having openings formed therein at one end thereof, each being large enough to allow the spring-like engagement portion of the stopper to pass; drill blade insertion paths formed at the other end thereof to be open at the top thereof, each being large enough to allow the drill blade to pass; concave parts formed therein extending from the respective opening to the drill blade insertion path and being capable of storing stoppers different in length from each other respectively; a protrusion formed in each of the concave parts to be engaged in a groove formed in the outer peripheral surface of the stopper; and stopper holding overhangs formed at the top of each concave part and which is elastic enough not to interfere with insertion of the stopper from above into the concave part and removal of the stopper from inside the concave part to above.

In the stopper storage case according to the present invention, the ends of the openings of the concave parts should preferably be positioned in a line to facilitate selection of a desired one of the stoppers stored in the concave parts. In case the concave part is formed rectangular in cross section, the protrusion may be provided on both side faces of the concave part. In case the concave part is formed semicircular in cross section, the protrusion may be provided on the bottom of the concave part. In case the stopper holding overhang is formed from the same material as that of the case body, the material of the stopper storage case may be elastic enough to allow the opening of the concave part to increase in area when the stopper is inserted from above into the concave part or when the stopper is ejected to above from inside the concave part. In case the stopper holding overhang is formed from an elastic material, such as elastomer, bonded and fixed on the top of the material of the case body, the case body may be formed from a material which may be approximately rigid. For the stopper storage case, an extension to enhance the stability of the stopper storage case may be provided either integrally with or separately from the case body at the sides of the drill blade insertion paths opposite to the openings of the stopper storage case and the extension should preferably be cut out at a portion thereof corresponding to extension of at least each concave part. Owing to this arrangement, when the drill installed to the dental handpiece is moved toward the spring-like engagement portion of the stopper received in the concave part in the stopper storage case, the blade of the drill is inserted and passed through the through-hole in the stopper until the drill blade is positioned in the drill blade insertion path, the flange projecting from the shank of the drill is pushed and engaged in the spring-like engagement portion of the stopper and then the dental handpiece is raised away from the stopper storage case to move the stopper to above from inside the concave part against the elasticity of the projecting stopper holding overhang, the cutout will prevent the free end of the drill blade projecting out of the drill blade insertion path from getting in touch with the extension. In case this extension is provided, there should preferably be provided on the case body side by side with the concave part a measuring concavity having a portion the end of the stopper at the side of the blade of the drill will abut when the stopper, having forced and engaged in the spring-like engagement portion thereof the projecting flange on the shank of the drill installed to the dental handpiece, is inserted from the top, or through the opening, of the case body, and also there should preferably provided on the extension a scale which reads a length from the drill blade-side end of the stopper to the free end of the blade of the drill. These two features will advantageously contribute to the usability of the stopper storage case. Also, the stopper storage case should preferably be formed from a material which can resist the heat during autoclaved sterilization. Because of this heat resistance, the stopper storage case may be subjected to autoclaved sterilization with the stoppers having been used being kept therein. Further, the stoppers will not get scattered and lost at the time of washing, sterilization or autoclaved sterilization.

In the stopper storage case according to the present invention for storing in parallel a plurality of stoppers each formed as a cylinder in which a drill, used in dental implant treatment to bore a dental implant fixture embedding hole in the jawbone, is to be fitted first at the free end of the blade thereof, the stopper including a spring-like engagement portion which is to be engaged on a projecting flange provided on a shank of the drill to thereby define a penetration depth of the drill, the stopper storage case has openings formed therein at one end thereof, each being large enough to allow the spring-like engagement portion of the stopper to pass; drill blade insertion paths formed at the other end thereof to be open at the top thereof, each being large enough to allow the drill blade to pass; concave parts formed therein extending from the respective opening to the drill blade insertion path and being capable of storing stoppers different in length from each other respectively; a protrusion formed in each of the concave parts to be engaged in a groove formed in the outer peripheral surface of the stopper; and stopper holding overhangs formed at the top of each concave part and which is elastic enough not to interfere with insertion of the stopper from above into the concave part and removal of the stopper from inside the concave part to above. Owing to this structure of the stopper storage case, the stopper can be attached to the drill installed to the dental handpiece simply by moving the drill installed to the dental handpiece from he opening toward the stopper received in the concave part with the spring-like engagement portion being positioned at the opening while being retained by the stopper holding overhang not to be disengaged to above and by the protrusion not to be disengaged through the opening, inserting the blade of the drill through the through-hole in the stopper to pass by the drill blade insertion path, thus forcing and engaging the projecting flange on the drill shank into the spring-like engagement portion of the stopper, and then raising the stopper to above from inside the concave part and drill blade insertion path against the elasticity of the stopper holding overhang. Also, the stopper can be detached from the drill installed to the dental hand piece simply by inserting the stopper from above into the concave part with the drill blade being positioned in the drill blade insertion path and the spring-like engagement portion of the stopper being positioned at the side of the opening and moving the dental handpiece away from the opening. Then the protrusion formed inside the concave part will be engaged in the groove on the outer peripheral surface of the stopper, so that the stopper will not be movable to the opening. The flange projecting from the shank of the drill comes out, only the stopper stays inside the concave part, and thus the stopper can be detached from the drill installed to the dental handpiece.

As above, attaching and detaching the stopper to and from the drill can be effected inside the stopper storage case. So, the stoppers will not be scattered and lost. Also, since the protrusion formed in the concave part is engaged in the groove formed in the outer peripheral surface of the stopper to block the stopper from moving to the opening and the stopper is also movable to above under the elasticity of the stopper holding overhang formed at the upper side of the concave part, the stoppers stored in the concave parts formed in the stopper storage case can be held there and kept for easy finding one of the stoppers that defines a desired penetration depth of the drill blade.

In the aforementioned stopper storage case, the ends of the openings of the concave parts may be provided in a line. With this arrangement, a desired one can be selected more easily from among the stoppers thus received. In case the concave part is formed rectangular in cross section, the protrusion may be provided on both side faces of the concave part. Also, in case the concave part is formed semicircular in cross section, the protrusion may be provided on the bottom of the concave part. In case the stopper holding overhang is formed from the material used to form the body of the stopper storage case, the material of the stopper storage case may be a one having a sufficient elasticity to allow the opening of the concave part to increase in area when the stopper is inserted from above into the concave part or when the stopper is ejected to above from inside the concave part. Further, in case the stopper holding overhang is formed from an elastic material, such as elastomer, and fixed by bonding to the top of a material forming the body of the stopper storage case, the case body may be formed from a material which may be approximately rigid. For the stopper storage case there may also be provided an extension to enhance the stability of the stopper storage case. The extension is provided either integrally with or separately from the case body at the sides of the drill blade insertion paths opposite to the openings of the stopper storage case and the extension is cut out at a portion thereof which will be covered by at least concave parts if the latter are extended. In this case, when moving the drill installed to the dental handpiece toward the spring-like engagement portion of the stopper received in the concave part in the stopper storage case, inserting and passing the blade of the drill through the through-hole in the stopper until the drill blade goes into the drill blade insertion path, forcing and engaging the projecting flange on the shank of the drill into the spring-like engagement path and then raising the dental handpiece away from the stopper storage case to move the stopper to above from inside the concave part against the elasticity of the projecting stopper-holding overhang, the cutout will prevent the free end of the blade of the drill projecting out of the drill blade insertion path from getting in touch with the extension. In case this extension is provided, a measuring concavity may be provided on the case body side by side with the concave part. When the stopper, having forced and engaged in the spring-like engagement portion thereof the projecting flange on the shank of the drill installed to the dental handpiece, is inserted from the top, or through the opening, of the case body, the end of the stopper at the side of the blade of the drill abuts a portion of the measuring concavity. Also, there may be provided on the extension a scale which reads a length from the end of the stopper at the side of the blade to the free end of the blade of the drill. These two features will advantageously contribute to the usability of the stopper storage case. The extension should preferably be provided separately from of the case body so as to be removably installable to the latter. In this case, the stopper storage case and extension are easier to clean, sterilize and store. Also, the stopper storage case may be formed from a material which can resist a heat at the time of autoclaved sterilization. Because of this heat resistance, the stopper storage case may be subjected to autoclaved sterilization while the stoppers having been used are being kept therein. Further, the stoppers will not get scattered and lost at the time of autoclaved sterilization.

The foregoing and other features, aspects and advantages of the present invention will become more apparent from the following detailed description of embodiments of the present invention when taken in conjunction with the accompanying drawings. It should be noted that the present invention is not limited to the embodiments but can freely be modified without departing from the scope and spirit thereof defined in the claims given later.

DETAILED DESCRIPTION OF THE PREFERRED EMBODIMENTS

Figure 1:
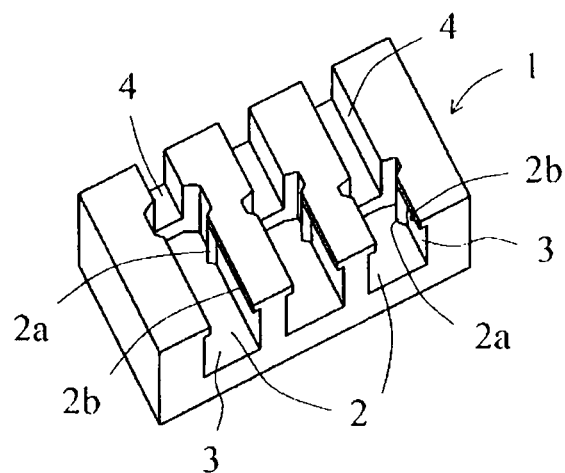
FIG. 1 is a perspective view of an embodiment of the stopper storage case according to the present invention.
Figure 2:
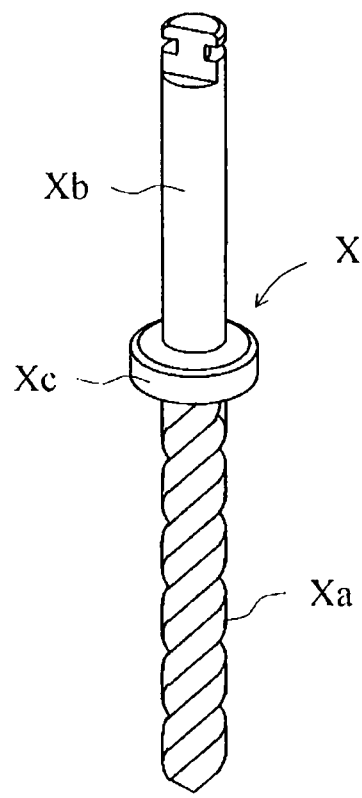
FIG. 2 is also a perspective view explaining, as an example, a drill having a projecting flange installed on a shank thereof and which is used to bore a dental implant fixture embedding hole in the jawbone in the implant surgery.
Figure 3:
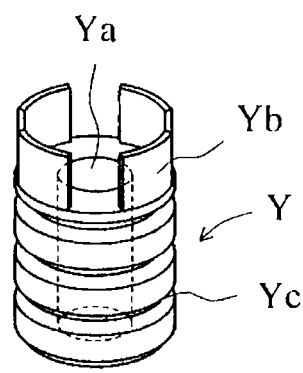
FIG. 3 is a perspective view explaining, as an example, a stopper having a spring-like engagement portion which is to be engaged on the projecting flange fitted onto the drill shank first at the free end of a blade of the drill shown in FIG. 2 and which thus defines a penetration depth of the drill blade.
Figure 4:
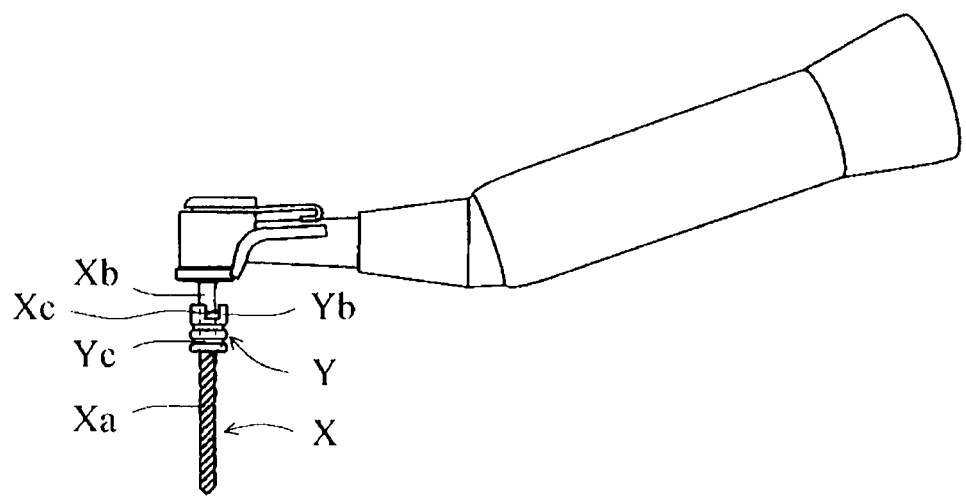
FIG. 4 is a perspective view of the drill in FIG. 2 having the stopper in FIG. 3 installed thereon and which is attached to a dental handpiece.
Figure 5:
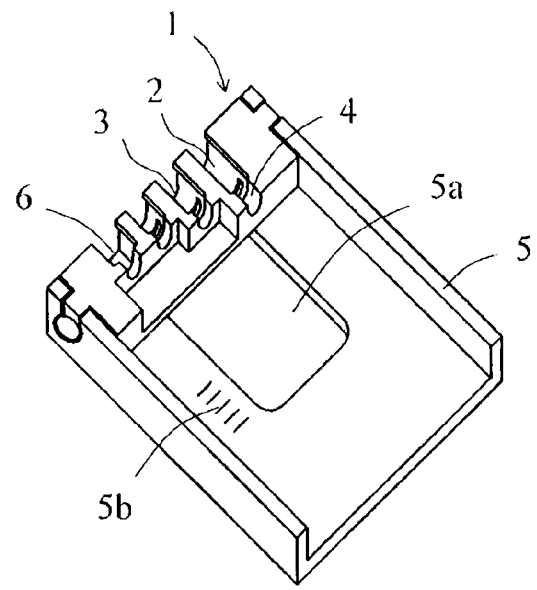
FIG. 5 is a perspective view of another embodiment of the stopper storage case according to the present invention.
Figure 6:
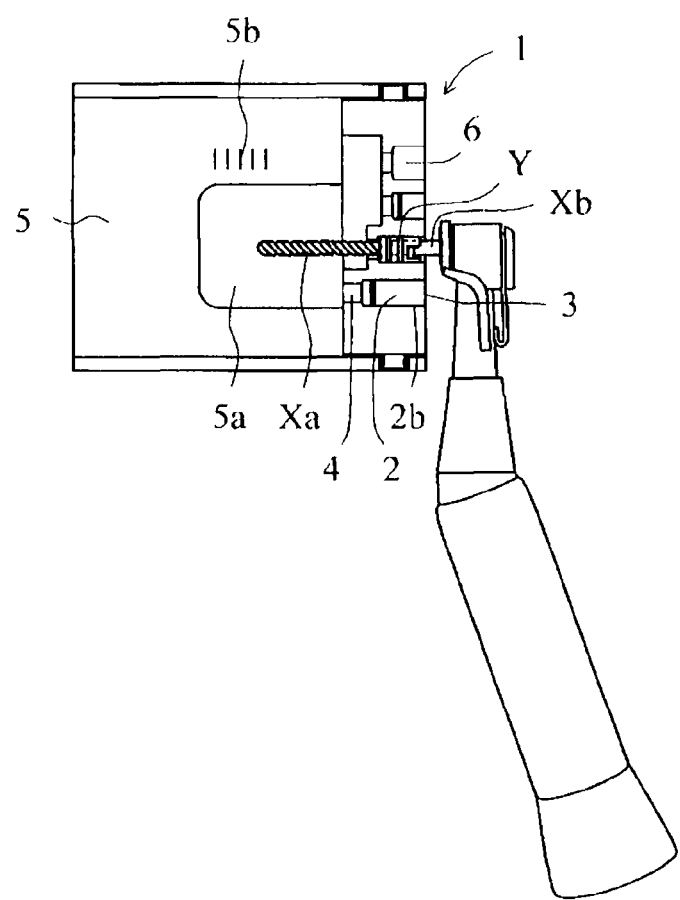
FIG. 6 is a perspective view of the stopper storage case, showing that the dental handpiece to which the drill having the stopper in FIG. 4 attached thereto is attached is set in place in the stopper storage case in FIG. 5 according to the present invention.

The present invention will be described in detail below concerning the embodiments thereof.

In Figures, the reference symbol X indicates a drill used in the field of dental implant surgery. As shown, the drill X has a blade Xa to bore a dental implant fixture embedding hole in the jawbone. The drill X includes also a shank Xb and a projecting flange Xc provided on the shank Xb.

The reference symbol Y indicates a stopper formed as a cylinder having formed herein a through-hole Ya into which the drill X is to be fitted first at the free end of the drill blade Xa. The stopper Y includes also a spring-like engagement portion Yb which is engaged on the flange Xc on the shank Xb of the drill X. The stopper Y designed as above defines a penetration depth of the blade Xa. Since the spring-like engagement portion Yb is required to widen once as it is engaged on the flange Xc of the drill X and restore its initial state under the action of its elasticity, it has several slits formed therein in parallel with the through-hole Ya. The stopper Y further has grooves Yc formed circumferentially at intervals of a predetermined length on the cylindrical surface contiguous to the spring-like engagement portion Yb.

The reference numeral 1 indicates the stopper storage case according to the present invention. As shown, the stopper storage case 1 has formed at one end thereof openings 3 each large enough to receive the spring-like engagement portion Yb of the stopper Y and at the other end thereof drill blade insertion paths 4 each formed open at the top thereof to receive the blade Xa of the drill X. Between the opening 3 and drill blade insertion path 4 there is defined a concave part 2 in which the stopper Y is to be received. The concave parts 2 are different in length (from the opening 3 to the drill blade insertion path 4) from each other to receive stoppers Y different in length from each other, respectively. Each of the concave parts 2 has formed therein a protrusion 2a which is engaged in the groove Yc formed on the outer peripheral surface of the stopper Y. Also, on either upper lateral side of each concave part 2 there is formed a stopper holding overhang 2b having such elasticity that it will not interfere with insertion of the stopper Y from above into the concave part 2 and ejection of the stopper Y to above from inside the concave part 2.

In the aforementioned stopper storage case 1, the ends of the openings 3 of the concave parts 2 should preferably be in a line. With this arrangement, the ends of the spring-like engagement portions Yb of the stoppers Y received in the respective concave parts 2 of the stopper storage case 1 are in a line so that a desired one of the stoppers Y thus received can be selected more easily. In case the concave part 2 is formed rectangular in cross section, the protrusion 2a may be provided on both side faces of the concave part 2. Also, in case the concave part 2 is formed semicircular in cross section, the protrusion 2a may be provided on the bottom of the concave part 2. In case the stopper holding overhang 2b is formed from the same material as that of the body of the stopper storage case 1, the material of the stopper storage case 1 may be a one having a sufficient elasticity to allow the opening of the concave part 2 to increase in area when the stopper is inserted from above into the concave part 2 or when the stopper Y is ejected to above from inside the concave part 2. Further, in case the stopper holding overhang 2b is formed from an elastic material, such as elastomer, and fixed by bonding to the top of a material forming the body of the stopper storage case 1, the case body may be formed from a material which may be approximately rigid.

For the stopper storage case 1, there may also be provided an extension 5 to enhance the stability of the stopper storage case 1. The extension 5 may be provided either integrally with or separately from the case body at the sides of the drill blade insertion paths 4 opposite to the openings 3 of the stopper storage case 1 and the extension 5 is cut out at a portion (indicated with the numeral 5a) thereof which will be covered by at least the concave parts 2 when the latter are extended. When the drill X installed to the dental handpiece is moved toward the spring-like engagement portion Yb of the stopper Y received in the concave part 2 in the stopper storage case 1, the blade Xa of the drill X is inserted and passed through the through-hole Ya in the stopper Y until the drill blade Xa goes into the drill blade insertion path 4, the projecting flange Xc on the shank Xb of the drill X is forced and engaged into the spring-like engagement portion Yb and then the dental handpiece is raised away from the stopper storage case 1 to move the stopper Y to above from inside the concave part 2 against the elasticity of the projecting stopper holding overhang 2b, the cutout 5a will prevent the free end of the blade Xa of the drill X projecting out of the drill blade insertion path 4 from getting in touch with the extension 5. In case this extension 5 is thus provided, a measuring concavity 6 may be provided on the case body side by side with the concave part 2. When the stopper Y, having forced and engaged in the spring-like engagement portion Yb thereof the projecting flange Xc on the shank Xb of the drill X installed to the dental handpiece, is inserted from the top, or through the opening, of the case body, the end of the stopper Y at the side of the blade Xa of the drill X abuts a portion of the measuring concavity 6. Also, there may be provided on the extension 5 a scale 5b which reads a length from the end of the stopper Y at the side of the blade Xa to the free end of the blade Xa of the drill X. These two features will advantageously contribute to the usability of the stopper storage case 1. The extension 5 should preferably be provided separately from the case body so as to be removably installable to the latter. In this case, the stopper storage case 1 and extension 5 are easier to clean, sterilize and store.

To attach the stopper Y to the drill X installed to the dental handpiece by the use of the stopper storage case 1 according to the present invention, the drill X installed to the dental handpiece is moved toward the stopper Y received in the concave part 2 while being blocked by the stopper holding overhang 2b from being disengaged to above and by the protrusion 2a from being disengaged through the opening 3, the blade Xa of the drill X is inserted and passed through the through-hole Ya in the stopper Y until the projecting flange Xc on the shank Xb of the drill X is pushed and engaged in the spring-like engagement portion Yb of the stopper Y, and then the stopper Y is pulled out of the concave part 2 and drill blade insertion path 4 against the elasticity of the stopper holding overhang 2b.

To detach the stopper Y from the drill X installed to the dental handpiece by means of the stopper storage case 1, the stopper Y is inserted from above into the concave part 2 so that the blade Xa of the drill X positions itself in the drill blade insertion path 4 and spring-like engagement portion Yb of the stopper Y is positioned at the side of the opening 3 and then the dental handpiece is moved away from the opening 3. In this condition, the protrusion 2a formed in the stopper path 2 is engaged in the groove Yc formed in the outer peripheral surface of the stopper Y to stop the stopper Y from moving toward the opening 3. Therefore, the flange Xc projecting from the shank Xb of the drill X is disengaged from the spring-like engagement portion Yb while only the stopper Y is staying in the concave part 2, and thus the stopper Y can be detached from the drill X being installed to the dental handpiece.

As mentioned above, to enhance the stability of the stopper storage case 1, the extension 5 is provided either integrally with or separately from the case body at the side of the drill blade insertion path 4 opposite to the opening 3 of the stopper storage case 1. Also, the measuring concavity 6 is provided on the case body side by side with the concave parts 2, and there is provided on the extension 5 the scale 5b which reads a length from the end of the stopper Y at the side of the blade Xa to the free end of the blade Xa of the drill X. By inserting from the top, or through the opening, of the case body, the stopper Y having pushed and engaged in the spring-like engagement portion Yb thereof the projecting flange Xc on the shank Xb of the drill X installed to the dental handpiece until it is put in contact with a portion of the measuring concavity 6 with which the end face of the stopper Y at the side of the drill blade Xa is in contact, the length from the end face of the stopper Y at the side of the blade Xa to the end face of the blade Xa of the drill X can be read easily on the scale 5b. As mentioned above, these features are very advantageous for the usability of the stopper storage case 1.

When the stoppers Y are to be kept unused, they can be stored in the respective concave parts 2 of the stopper storage case 1 according to the present invention in such a manner that their spring-like engagement portions Yb are positioned at the side of the openings 3. The stopper Y thus positioned is not movable since the protrusion 2a formed in the concave part 2 is engaged in the groove Yc formed in the outer peripheral surface of the stopper Y. Also, since the stopper holding overhang 2b projecting laterally from the top of the concave part 2 prevents the stopper Y from being easily disengaged from inside the concave part 2 to above, the stopper Y can be stably stored in the stopper storage case 1. Also, the stopper storage case 1 may be formed from a material which can resist a heat at the time of autoclaved sterilization. Because of this heat resistance, the stopper storage case 1 may be subjected to autoclaved sterilization while the stoppers having been used are being kept therein. Further, the stoppers Y will not get scattered and lost at the time of autoclaved sterilization.

What is claimed is:

1. A stopper storage case, comprising:
   a case body having a first end, sides, and a second end, which is opposite from the first end of the case body;
   a plurality of parallel openings formed in the first end of the case body;
   a plurality of parallel drill blade insertion paths formed in the second end of the case body;
   concave parts of different lengths formed between respective openings and drill blade insertion paths of the case body such that each concave part together with a respective opening and drill blade insertion path forms a through-hole from the first end of the case body to the second end of the case body, wherein each concave part comprises a protrusion on an inner surface thereof and a stopper holding overhang at the top of each concave part; and (Y) a plurality of stoppers each formed as a cylinder having a first end and a second end opposite to the first end, and each comprising
- (Ya) a stopper through-hole formed between the first end and the second end of the stopper,
- (Yb) a spring engagement portion at the first end of the stopper, and
- (Yc) a groove formed in the outer peripheral surface of the stopper, wherein the protrusion of the inner surface of the concave part is engaged with the groove (Yc) formed in the outer peripheral surface of the stopper, wherein the stopper storage case is configured such that when a drill (X) comprising a blade (Xa) at a free end, a shank (Xb) at the other end, and a projecting flange (Xc) disposed between the blade (Xa) and the shank (Xb) is inserted into the opening of the case body, the blade (Xa) of the drill passes through the stopper through-hole (Ya) and the drill blade insertion path at the second end of the case body, and the projecting flange (Xc) of the drill engages the spring engagement portion (Yb) of the stopper thereby defining a penetration depth of the blade (Xa).

2. The stopper storage case of claim 1, wherein the ends of the openings of the concave parts are positioned in a line.

3. The stopper storage case of claim 1, wherein the concave part has a rectangular cross section and the protrusions are formed on both side faces of the concave part.

4. The stopper storage case of claim 1, wherein the concave part has a semicircular cross section and the protrusions are formed on the bottom of the concave part.

5. The stopper storage case of claim 1, wherein the stopper holding overhang is formed from the material from which the case body is formed.

6. The stopper storage case of claim 1, wherein the stopper holding overhang is formed from an elastic material bonded and fixed on the top of a material of the case body, and wherein the case body is formed from a rigid material.

7. The stopper storage case of claim 1, further comprising:
an extension, which is provided either integrally with or separately from the case body at the sides of the drill blade insertion paths on the second end of the case body, wherein the extension comprises a cut out portion which will be covered by at least concave parts if the concave parts are extended.

8. The stopper storage case of claim 7, further comprising:
a measuring concavity comprising a further opening parallel with the plurality of openings formed in the first end of the case body, a further drill blade insertion path parallel with the drill blade insertion paths formed in the second end of the case body, and a further concave part connecting the further opening and the further drill blade insertion path of the measuring concavity; and a scale on the extension, wherein the scale on the extension reads a length from the second end of the stopper to the free end of the blade (Xa) of the drill when the drill (X) is inserted through the measuring concavity opening and the stopper through-hole (Ya) such that the projecting flange (Xc) of the drill abuts the spring engagement portion (Yb) of the stopper and the spring engagement portion is engaged with force.

9. The stopper storage case of claim 1, wherein the stopper case is formed from a material capable of resisting the heat during autoclaved sterilization.

* * * * *